(12) United States Patent
Klaes et al.

(10) Patent No.: US 7,244,716 B2
(45) Date of Patent: Jul. 17, 2007

(54) PHARMACEUTICAL COMPOSITION OF ANTIVIRAL AGENTS

(75) Inventors: Heinz-Gerd Klaes, Gau-Bickelheim (DE); Elena Koundourakis, Danbury, CT (US); Hernan Valdez, Somers, NY (US); Douglas Lytle Mayers, Newtown, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/809,060

(22) Filed: Mar. 25, 2004

(65) Prior Publication Data

US 2004/0235779 A1 Nov. 25, 2004

(30) Foreign Application Priority Data

| Mar. 27, 2003 | (EP) | ................... 03007001 |
| Jul. 17, 2003 | (EP) | ................... 03016224 |
| Dec. 20, 2003 | (EP) | ................... 03029507 |

(51) Int. Cl.
*A01N 43/04* (2006.01)
*A61K 31/70* (2006.01)
*C07H 19/00* (2006.01)
*C07H 19/048* (2006.01)

(52) U.S. Cl. .................... 514/49; 514/42; 514/45; 514/43

(58) Field of Classification Search .................. 514/42, 514/43, 45, 49
See application file for complete search history.

(56) References Cited

U.S. PATENT DOCUMENTS 6,147,095 A 11/2000 Ferry et al.

2001/0036920 A1 * 11/2001 Hirschman .................... 514/14

FOREIGN PATENT DOCUMENTS

| WO | WO 88/00050 | 1/1988 |
| WO | WO 91/01137 | 2/1991 |
| WO | WO 99/09031 | 2/1999 |
| WO | WO 99/41268 | 8/1999 |
| WO | WO 00/51641 | 9/2000 |

OTHER PUBLICATIONS

Roy M. Gulick et al; New drugs for HIV therapy; AIDS (2002) vol. 16 No. 4 pp. S135-S144; Lippincott Williams & Wilkins.
Erik De Clercq; New Developments in Anti-HIV Chemotherapy; Current Medicinal Chemistry (2001) vol. 8 pp. 1543-1572; Bentham Science Publishers Ltd.

* cited by examiner

*Primary Examiner*—Patrick Lewis
(74) *Attorney, Agent, or Firm*—Michael P. Morris; Mary-Ellen M. Devlin

(57) ABSTRACT

In accordance with the present invention there is provided a pharmaceutical composition useful for the treatment or prophylaxis of viral infections comprising tipranavir and at least one antiviral active compound of formula (I)

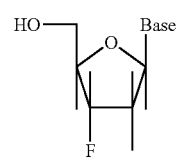

wherein Base is selected from the group consisting of thymine, cytosine, adenine, guanine, inosine, uracil, 5-ethyluracil and 2,6-diaminopurine, or a pharmaceutically acceptable salt or prodrug thereof.

20 Claims, No Drawings

PHARMACEUTICAL COMPOSITION OF ANTIVIRAL AGENTS

RELATED APPLICATIONS

This application claims priority to European Application No. 03029507.5, filed Dec. 20, 2003; European Application No. 03016224.2, filed Jul. 17, 2003; and European Application No. 03007001.5, filed Mar. 27, 2003, each of which is hereby incorporated by reference in its entirety.

FIELD OF THE INVENTION

The present invention relates to a pharmaceutical composition useful for the treatment of viral infections comprising tipranavir and at least one antiviral active compound of formula (I). Furthermore the present invention relates to a use of tipranavir in combination or alternation with a compound of formula (I) in the prophylaxis or treatment of a viral infection in a patient. The present invention also relates to a use of tipranavir in combination with a compound of formula (I) for the manufacture of a medicament for the prophylaxis or treatment of a viral infection in a patient. In addition the present invention relates to a kit of parts and to a manufacture for the prophylaxis or treatment of a viral infection in a patient.

BACKGROUND OF THE INVENTION

Human immunodeficiency virus (HIV) is recognized as the causative agent in AIDS.

Current therapies for HIV infection focus on inhibiting the activity of viral enzymes which are essential to the life cycle of the virus. The agents that are presently in use fall mainly into three classes, designated Nucleoside Reverse Transcriptase Inhibitors (NRTIs), Non-nucleoside Reverse Transcriptase Inhibitors (NNRTIs), and Protease Inhibitors (PIs). Presently, combination therapies, i.e. the selection of two or more antiretroviral agents taken together to make up a "drug cocktail," are the preferred treatment for HIV infection. Combination therapies have been shown to reduce the incidence of opportunistic infections and to increase survival time. Typically, the drug cocktail combines drugs from different classes, so as to attack the virus at several stages in the replication process. This approach has been shown to reduce the likelihood of the development of virus forms that are resistant to a given drug or class of drugs.

Treatment failure with rebound of the amount of HIV which can be measured in the blood is common for patients treated with combination antiretroviral regimens. Resistance to the drugs in the drug regimen develops as the virus replicates in the presence of these drugs. Because of structural similarities of the drugs within an antiretroviral class, cross resistance is commonly seen to the other members of that class (for example virologic failure on a regimen containing an NNRTI will lead to cross resistance to the other first generation NNRTI agents). As patients experience repeated virologic failure on antiretroviral combination therapy, their viruses develop broad multi-class antiretroviral drug resistance which limits the effectiveness of the next round of antiretroviral therapy. Many highly treatment experienced patients have been exposed to all three classes of antiretroviral drugs and cannot obtain two active drugs to form the core of a new, effective antiretroviral drug regimen.

Tipranavir is a known agent for the treatment of HIV infection.

Tipranavir, also known as U-140690 and PNU-140690, is an HIV protease inhibitor. Chemically, tipranavir is (6R)-3-((1R)-1-[3-({[5-trifluoromethyl)(2-pyridyl)]sulfonyl}amino)phenyl]propyl}-4-hydroxy-6-(2-phenylethyl)-6-propyl-5,6-dihydro-2H-pyran-2-one or ([R-(R*, R*)]-N-[3-[1-[5,6-dihydro-4-hydroxy-2-oxo-6-(2-phenylethyl)-6-prop yl-2H-pyran-3-yl]propyl]phenyl]-5-(trifluoromethyl)-2-pyridinesulfonamide) and has the following structural formula:

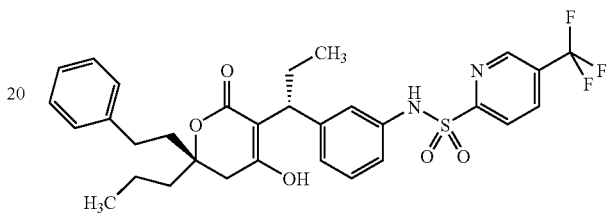

Tipranavir and methods for its synthesis and use in the treatment of HIV are described in WO 95/30670 and corresponding U.S. Pat. No. 5,852,195. Pharmaceutical formulations suitable for the oral administration of tipranavir are described in WO 99/06043 and WO 99/06044, and the corresponding U.S. Pat. Nos. 6,121,313 and 6,231,887.

As tipranavir is metabolized relatively rapidly by the cytochromes P450, especially the Cyp3A4 isoform, it is preferred to co-administer an inhibitor of Cyp3A4 in order to obtain therapeutically effective blood levels of tipranavir. The use of ritonavir for this purpose is described in U.S. Pat. No. 6,147,095. The use for this purpose of other inhibitors of Cyp3A4 is also possible.

Furthermore Compounds of the Formula (I)

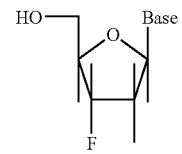

wherein Base is selected from the group consisting of thymine, cytosine, adenine, guanine, inosine, uracil, 5-ethyluracil and 2,6-diaminopurine, or a pharmaceutically acceptable salt or prodrug thereof, are described in the WO 88/00050 and WO 91/01137 for the therapeutic and prophylactic control and treatment of AIDS, HIV infections, hepatitis B virus (HBV) infections and retrovirus infections in animals and man. These nucleoside compounds are transformed by cells or enzymes to triphosphates which inhibit the reverse transcriptase of retrovirus as well as the activity of DNA dependent polymerase of hepatitis B virus.

Combinations of tipranavir with at least one compound of the formula (I) which exhibit potent therapeutic activity against HIV and HBV would greatly aid in the development of new combination therapy against human retroviral (HRV) infections and HBV.

SUMMARY OF THE INVENTION

In one aspect, the present invention provides a novel pharmaceutical composition useful for the treatment or prophylaxis of viral infections comprising tipranavir and at least one antiviral active compound of formula (I)

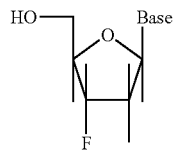

wherein Base is selected from the group consisting of thymine, cytosine, adenine, guanine, inosine, uracil, 5-ethyluracil and 2,6-diaminopurine, or a pharmaceutically acceptable salt or prodrug thereof.

The pharmaceutical compositions of the present invention are useful in therapy, in particular as antivirals, especially in the treatment or prophylaxis of human retroviral (HRV) infections.

In a second aspect, there is provided a use of tipranavir in combination or alternation with at least one antiviral active compound of formula (I)

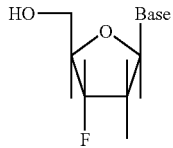

wherein Base is selected from the group consisting of thymine, cytosine, adenine, guanine, inosine, uracil, 5-ethyluracil and 2,6-diaminopurine, or a pharmaceutically acceptable salt or prodrug thereof, in the prophylaxis or treatment of a viral infection in a patient.

In a third aspect, there is provided a use of tipranavir in combination with at least one antiviral active compound of formula (I)

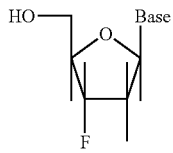

wherein Base is selected from the group consisting of thymine, cytosine, adenine, guanine, inosine, uracil, 5-ethyluracil and 2,6-diaminopurine, or a pharmaceutically acceptable salt or prodrug thereof, for the manufacture of a medicament for the prophylaxis or treatment of a viral infection in a patient.

In a fourth aspect of this invention, there is provided a kit of parts for the prophylaxis or treatment of a viral infection in a patient, comprising:

(a) a first containment containing a pharmaceutical composition comprising tipranavir and at least one pharmaceutically acceptable carrier, and
(b) a second containment containing a pharmaceutical composition comprising an antiviral active compound of formula (I)

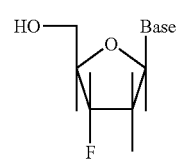

wherein Base is selected from the group consisting of thymine, cytosine, adenine, guanine, inosine, uracil, 5-ethyluracil and 2,6-diaminopurine, or a pharmaceutically acceptable salt or prodrug thereof, and at least one pharmaceutically acceptable carrier.

In a fifth aspect of this invention, there is provided a manufacture comprising tipranavir and at least one antiviral active compound of formula (I)

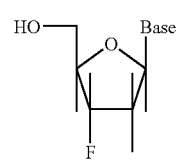

wherein Base is selected from the group consisting of thymine, cytosine, adenine, guanine, inosine, uracil, 5-ethyluracil and 2,6-diaminopurine, or a pharmaceutically acceptable salt or prodrug thereof, for use in combination or alternation in the prophylaxis or treatment of a viral infection in patient.

With the combination of tipranavir and a compound of the formula (I) according to this invention, including its use in prophylaxis and treatment, the person skilled in the art can achieve an advantageous therapeutic effect to inhibit viral replication, especially of human retrovirus (HRV) and HBV, in particular of multiresistant HIV. In most cases, the enhanced therapeutic effect is not attainable by administration of either agent alone. In a preferred but not necessary embodiment, the effect of administration of tipranavir and the compound of formula (I) in combination or alternation is synergistic. Even though a combination exhibits additive and not synergistic effects, the combination can still provide an effect that is different from the separate administration of the two agents. For example, the biodistribution, pharmacokinetics, cytotoxic effects or metabolism of one can be affected by the other.

Further aspects of the present invention become apparent to the one skilled in the art from the following detailed description and examples.

Definitions

The term "pharmaceutically acceptable salt" means a salt of the corresponding compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19, which is hereby incorporated by reference in its entirety.

As used herein, the term "treatment" means the administration of the antivirally active compounds according to this invention in combination or alternation according to the present invention to alleviate or eliminate symptoms of the viral infection and/or to reduce viral load in a patient.

As used herein, the term "prevention" or "prophylaxis" means the administration of the antivirally active compounds according to this invention in combination or alternation according to the present invention post-exposure of the individual to the virus but before the appearance of symptoms of the disease, and/or prior to the detection of the virus in the blood.

As used herein, the term "human retrovirus" (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses.

DETAILED DESCRIPTION OF THE INVENTION

The virally active agents according to this invention may be in either free form or in protected form at one or more of the remaining (not previously protected) carboxyl, amino, hydroxy, or other reactive groups. The protecting groups may be any of those known in the art. Furthermore, the virally active agents according to this invention may also be used as in form of their pharmacologically acceptable salts and/or hydrates.

According to the first aspect of this invention, there is provided a novel pharmaceutical composition useful for the treatment of viral infections comprising tipranavir and at least one antiviral active compound of formula (I), or a pharmaceutically acceptable salt or prodrug thereof.

The following known compounds constitute part of the invention as preferred compounds of the formula (I) to be combined with tipranavir:

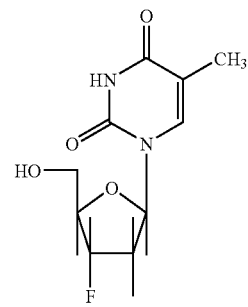

3'-deoxy-3'-fluorothymidine (FLT)

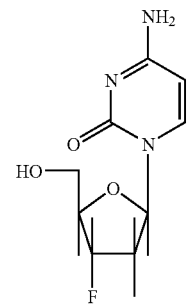

2',3'-dideoxy-3'-fluorocytidine

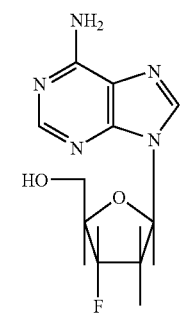

2',3'-dideoxy-3'-fluoroadenosine

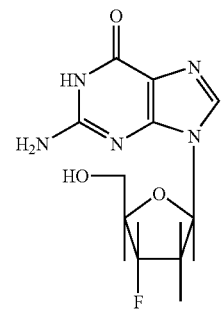

2',3'-dideoxy-3'-fluoroguanosine (FLG)

including pharmaceutically acceptable salts and prodrugs of the compounds listed above.

Preferred prodrugs of FLG are described in WO 99/09031 and WO 99/41268, which documents in their entirety are incorporated herein by reference.

The most preferred compound of the formula (I) to be combined with tipranavir according to the aspects of this invention is selected from the group consisting of:
(a) 3'-deoxy-3'-fluorothymidine, or a pharmaceutically acceptable salt or prodrug thereof, and
(b) 2',3'-dideoxy-3'-fluoroguanosine (FLG), or a pharmaceutically acceptable salt or prodrug thereof, in particular 3'-deoxy-3'-fluoro-5-O-[2-(L-valyloxy)-propionyl]guanosine, or a pharmaceutically acceptable salt thereof.

The compound of the formula (I) is very most preferably selected from the group consisting of 3'-deoxy-3'-fluorothymidine and 3'-deoxy-3'-fluoro-5-O-[2-(L-valyloxy)-propionyl]guanosine, including pharmaceutically acceptable salts thereof.

3'-deoxy-3'-fluoro-5-O-[2-(L-valyloxy)-propionyl]guanosine is a preferred prodrug of FLG and can be depicted by the following structure

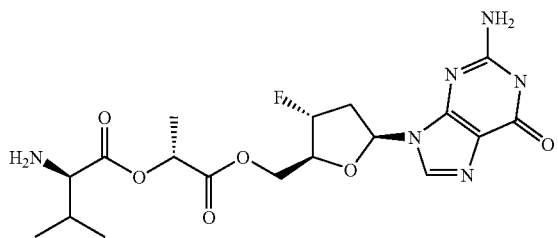

The synthesis of 3'-deoxy-3'-fluoro-5-O-[2-(L-valyloxy)-propionyl]guanosine, also named as 21,3'-dideoxy-3'-fluoro-5-O-[2-(L-valyloxy)-propionyl]guanosine, is described in the WO 99/09031 and especially in example 32 therein.

Therefore, a preferred pharmaceutical composition useful for the treatment of viral infections comprises tipranavir and 3'-deoxy-3'-fluorothymidine or 3'-deoxy-3'-fluoro-5-O-[2-(L-valyloxy)-propionyl]guanosine, or a pharmaceutically acceptable salt or prodrug thereof.

Furthermore, tipranavir in combination or alternation with preferably 3'-deoxy-3'-fluorothymidine or 3'-deoxy-3'-fluoro-5-O-[2-(L-valyloxy)-propionyl]guanosine, or a pharmaceutically acceptable salt or prodrug thereof, is used in the prophylaxis or treatment of a viral infection in a patient.

Also preferred is the use of tipranavir in combination with 3'-deoxy-3'-fluorothymidine or 3'-deoxy-3'-fluoro-5-O-[2-(L-valyloxy)-propionyl]guanosine, or a pharmaceutically acceptable salt or prodrug thereof, for the manufacture of a medicament for the prophylaxis or treatment of a viral infection in a patient.

A preferred kit of parts for the prophylaxis or treatment of a viral infection in a patient, comprises:
(a) a first containment containing a pharmaceutical composition comprising tipranavir and a pharmaceutically acceptable carrier, and
(b) a second containment containing a pharmaceutical composition comprising 3'-deoxy-3'-fluorothymidine or 3'-deoxy-3'-fluoro-5-O-[2-(L-valyloxy)-propionyl]guanosine, or a pharmaceutically acceptable salt or prodrug thereof, and a pharmaceutically acceptable carrier.

A preferred manufacture comprises tipranavir and 3'-deoxy-3'-fluorothymidine or 3'-deoxy-3'-fluoro-5-O-[2-(L-valyloxy)-propionyl]guanosine, or a pharmaceutically acceptable salt or prodrug thereof, for use in combination or alternation in the prophylaxis or treatment of a viral infection in a patient.

The advantageous effects of the combination of tipranavir and the compound of formula (I) are realized over a wide ratio, like for example in a ratio of between 1:250 to 250:1.

Therefore, in the compositions, combinations, kit of parts, manufacture and/or the use of the combinations according to this invention, tipranavir and the at least one compound of formula (I) are preferably present in a synergistic ratio. Usually, this ratio is between about 1:250 to about 250:1. More preferably the ratio is between about 1:50 to about 50:1. The most preferred ratio is between about 1:20 to about 20:1, which includes the ratios 1:18, 1:16, 1:14, 1:12, 1:10; 1:8; 1:6; 1:5; 1:4; 1:3; 1:2,5; 1:2; 1:1,5; 1:1,2; 1:1; 1,2:1; 1,5:1; 2:1; 2,5:1; 3:1; 4:1; 5:1; 6:1; 8:1; 10:1, 12:1, 14:1, 16:1, 18:1 and all ranges in between.

If a further therapeutic agent is added, ratios will be adjusted accordingly.

It will be appreciated that the amount of pharmaceutical composition according to the invention required for use in treatment or prophylaxis will vary not only with the particular compound selected but also with the route of administration, the nature and severity of the condition for which treatment or prophylaxis is required, the age, weight and condition of the patient, concomitant medication and will be ultimately at the discretion of the attendant physician or veterinarian. In general however the active compounds are included in the pharmaceutically acceptable carrier in an amount sufficient to deliver to a patient a therapeutically effective amount of compound to inhibit viral replication in vivo, especially HIV replication, without causing serious toxic effects in the treated patient. By "inhibitory amount" is meant an amount of active ingredient sufficient to exert an inhibitory effect as measured by, for example, an assay such as the ones described herein. A suitable dose will preferably be in the range of from about 0.05 to about 200 mg/kg of body weight per day.

The desired dose may conveniently be presented in a single dose or as divided dose administered at appropriate intervals, for example as two, three, four or more doses per day.

The pharmaceutical composition according to the present invention is conveniently administered in unit dosage form; for example containing 5 to 3000 mg, conveniently 5 to 1000 mg of active ingredient(s) per unit dosage form.

The pharmaceutical acceptable carrier(s) must be "acceptable" in the sense of being compatible with the other ingredients of the formulation and not deleterious to the recipient thereof.

Examples of pharmaceutically acceptable carriers are magnesium stearate, chalk, starch, lactose, wax, gum or gelatin. Carriers which are suited to achieve a sustained release, for example natural or synthetic polymers or liposomes, are known to the one skilled in the art. Pharmaceutically acceptable carriers also comprise liquid carriers and diluents, for example water, alcohol, glycerine or oil, which serve as a base for liquid formulations, such as solutions, suspensions or emulsions.

The compositions referred to above may conveniently be presented for use in the form of a pharmaceutical formulation and therefore pharmaceutical formulations comprising a composition as defined above together with a pharmaceutically acceptable carrier comprise a further aspect of the invention.

The individual components of such compositions may be administered either in combination, i.e. simultaneously, or in alternation, i.e. sequentially, in separate or combined pharmaceutical formulations.

When tipranavir is used in combination with a compound of the formula (I) against the same virus the dose of each compound may be either the same as or differ from that when the compound is used alone. Appropriate doses will be readily appreciated by those skilled in the art.

The compositions according to this invention preferably also comprise at least one pharmaceutically acceptable carrier.

According to the third aspect of this invention, the combination of tipranavir and at least one compound of the formula (I) is used for the manufacture of a medicament for the prophylaxis or the treatment of a viral infection in a patient.

According to one embodiment, this medicament may be a unit dosage form, which is preferably useful in combination therapy, such as capsules or tablets. The unit dosage form contains a pharmaceutical composition according to this invention, i.e. tipranavir in combination with at least one compound of the formula (I), with at least one pharmaceutically acceptable carrier.

Therefore, another object of this invention also comprises bringing tipranavir and at least a compound of the formula (I) together in conjunction or association with a pharmaceutically acceptable carrier.

According to another embodiment, this medicament is a multiple dosage form, preferably a kit of parts, which is especially useful in alternation and/or combination therapy to flexibly suit the individual therapeutic needs of the patient.

It is known, e.g. WO 00/25784, that various doses of ritonavir have substantial and significant effects on tipranavir by elevating, or enhancing, plasma concentrations of tipranavir. This pharmacokinetic drug interaction may offer the following advantages:

enhanced antiviral activity of tipranavir,
reduction of the administered tipranavir dose,
improved safety profile.

Therefore, according to one embodiment the combinations, compositions, kit of parts, manufactures of this invention and the uses thereof, which comprise tipranavir and at least one compound of the formula (I), or a pharmaceutically salt or prodrug thereof, further comprise ritonavir.

Following this, a preferred pharmaceutical composition useful for the treatment of viral infections comprises tipranavir in combination with ritonavir and 3'-deoxy-3'-fluorothymidine or 3'-deoxy-3'-fluoro-5-O-[2-(L-valyloxy)-propionyl]guanosine, or a pharmaceutically acceptable salt or prodrug thereof.

Furthermore, tipranavir in combination with ritonavir and in combination or alternation with preferably 3'-deoxy-3'-fluorothymidine or 3'-deoxy-3'-fluoro-5-O-[2-(L-valyloxy)-propionyl]guanosine, or a pharmaceutically acceptable salt or prodrug thereof, is used in the prophylaxis or treatment of a viral infection in a patient.

Also preferred is the use of tipranavir in combination with ritonavir and 3'-deoxy-3'-fluorothymidine or 3'-deoxy-3'-fluoro-5-O-[2-(L-valyloxy)-propionyl]guanosine, or a pharmaceutically acceptable salt or prodrug thereof, for the manufacture of a medicament for the prophylaxis or treatment of a viral infection in a patient.

A preferred kit of parts for the prophylaxis or treatment of a viral infection in a patient, comprises:

(a) a first containment containing a pharmaceutical composition comprising tipranavir and ritonavir and a pharmaceutically acceptable carrier, and (b) a second containment containing a pharmaceutical composition comprising 3'-deoxy-3'-fluorothymidine or 3'-deoxy-3'-fluoro-5-O-[2-(L-valyloxy)-propionyl]guanosine, or a pharmaceutically acceptable salt or prodrug thereof, and a pharmaceutically acceptable carrier.

Another preferred kit of parts for the prophylaxis or treatment of a viral infection in a patient, comprises:

(a) a first containment containing a pharmaceutical composition comprising tipranavir and a pharmaceutically acceptable carrier, and (b) a second containment containing a pharmaceutical composition comprising ritonavir and a pharmaceutically acceptable carrier, and (c) a third containment containing a pharmaceutical composition comprising 3'-deoxy-3'-fluorothymidine or 3'-deoxy-3'-fluoro-5-O-[2-(L-valyloxy)-propionyl]guanosine, or a pharmaceutically acceptable salt or prodrug thereof, and a pharmaceutically acceptable carrier.

A preferred manufacture comprises tipranavir, ritonavir and a compound of the formula (I) selected from the group consisting of 3'-deoxy-3'-fluorothymidine or 3'-deoxy-3'-fluoro-5-O-[2-(L-valyloxy)-propionyl]guanosine, or a pharmaceutically acceptable salt thereof, for use in combination or alternation in the prophylaxis or treatment of a viral infection in a patient.

In said combinations, compositions, kit of parts, manufactures, which comprise tipranavir, ritonavir and at least one compound of the formula (I) the ratio and the amount of tipranavir and ritonavir present in these combinations are preferably chosen to achieve therapeutically effective plasma levels of tipranavir. Upper limits, lower limits and therapeutically preferred areas of dosage regimens are known from scientific literature, e.g. WO 00/25784, and may be optimized in view of the combination with the compounds of the formula (I) according to known methods.

According to further embodiments the combinations, compositions, kit of parts, manufactures of this invention and the uses thereof comprise a combination selected from the group consisting of:

a compound of the formula (I), tipranavir and one, two or more further NRTIs;

a compound of the formula (I), tipranavir, a NNRTI and optionally one, two or more further NRTIs;

a compound of the formula (I), tipranavir, an entry inhibitor and optionally one, two or more further NRTIs;

a compound of the formula (I), tipranavir, a NNRTI, an entry inhibitor and optionally one, two or more further NRTIs;

a compound of the formula (I), tipranavir, an integrase inhibitor and optionally one, two or more further NRTIs;

a compound of the formula (I), tipranavir, a NNRTI, an integrase inhibitor and optionally one, two or more further NRTIs.

In the above listed combinations, compositions, kit of parts, manufactures and uses thereof tipranavir may advantageously be combined with ritonavir as described hereinbefore.

In the foregoing and in the following, the term "further NRTI" refers to a nucleoside reverse transcriptase inhibitor, or a pharmaceutically acceptable salt or prodrug thereof, other than the selected compound of the formula (I). Examples of further NRTIs are Abacavir Sulfate (Ziagen), Didanosine (ddI, Videx), Emtricitabine (Emtriva), Lamivudine (3TC, Epivir), Stavudine (d4t, Zerit), Tenofovir disoproxil fumarate (nucleotide, bis (POC) PMPA, Viread), Zalcitabine (ddc, Hivid), Zidovudine (AZT, Retrovir), Amdoxovir (DAPD; Gilead Sciences), Elvucitabine (ACH-126443; Achillion Pharm.), GS-7340 (Gilead Sciences), INK-20 (thioether phospholipid formulation of AZT; Kucera Pharm.), MIV-310 (Medivir AB), MIV-210 (Medivir AB), Racivir (racemic FTC; Pharmasset), Reverset (RVT, D-D4FC, DPC-817; Pharmasset), SPD-754 ((−)dOTC; Shire Pharm), BCH-13520 (Shire Pharm) and BCH-10618 (Shire Pharm).

In the foregoing and in the following, the term "NNRTI" refers to a non nucleoside reverse transcriptase inhibitor, or a pharmaceutically acceptable salt or prodrug thereof. Examples of NNRTIs are Delavirdine (Rescriptor), Efavirenz (DMP-266, Sustiva), Nevirapine (BIRG-587, Viramune), (+)-Calanolide A and B (Advanced Life Sciences), Capravirine (AG1549, S-1153; Pfizer), GW-695634 (GW-8248; GSK), MIV-150 (Medivir), MV026048 (R-1495; Medivir AB/Roche), NV-05 (Idenix Pharm.), R-278474 (Johnson & Johnson), RS-1588 (Idenix Pharm.), TMC-120/125 (Johnson & Johnson), TMC-125 (R-165335; Johnson & Johnson), UC-781 (Biosyn Inc.) and YM-215389 (Yamanoushi).

In the foregoing and in the following, the term "entry inhibitor" refers to an entry inhibitor, including fusion inhibitors, inhibitors of the CD4 receptor, inhibitors of the CCR5 co-receptor and inhibitors of the CXCR4 co-receptor, or a pharmaceutically acceptable salt or prodrug thereof. Examples of entry inhibitors are AMD-070 (AMD-11070; AnorMed), BlockAide/CR (ADVENTRX Pharm.), BMS 806 (BMS-378806; BMS), Enfurvirtide (T-20, R698, Fuzeon), KRH-1636 (Kureha Pharmaceuticals), ONO-4128 (GW-873140, AK-602, E-913; ONO Pharmaceuticals), Pro-140 (Progenics Pharm), PRO-542 (Progenics Pharm.), SCH-D (SCH-417690; Schering-Plough), T-1249 (R724; Roche/Trimeris), TAK-220 (Takeda Chem. Ind.), TNX-355 (Tanox) and UK-427,857 (Pfizer).

Examples of integrase inhibitors are L-870810 (Merck & Co.), c-2507 (Merck & Co.) and S(RSC)-1838 (Shionogi/GSK).

According to still further embodiments the combinations, compositions, kit of parts, manufactures of this invention and the uses thereof comprise a combination selected from the group consisting of a compound of the formula (I), tipranavir and a further antiviral agent. In these still further embodiments tipranavir may advantageously be combined with ritonavir as described hereinbefore.

A further antiviral agent may be selected from the group of the maturation inhibitors, antisense compounds or protease inhibitors, other than tipranavir. Examples of further antivirals are PA-457 (Panacos), KPC-2 (Kucera Pharm.), HGTV-43 (Enzo Biochem), Amprenavir (VX-478, Agenerase), Atazanavir (Reyataz), Indinavir Sulfate (MK-639, Crixivan), Lexiva (fosamprenavir calcium, GW-433908 or 908, VX-175), Lopinavir+Ritonavir (ABT-378/r, Kaletra), Nelfinavir Mesylate (Viracept), Saquinavir (Invirase, Fortovase), AG-1776 (JE-2147, KNI-764; Nippon Mining Holdings), AG-1859 (Pfizer), DPC-681/684 (BMS), GS224338 ('4338; Gilead Sciences), KNI-272 (Nippon Mining Holdings), Nar-DG-35 (Narhex), P(PL)-100 (P-1946; Procyon Biopharma), P-1946 (Procyon Biopharma), R-944 (Hoffmann-LaRoche), RO-0334649 (Hoffmann-LaRoche), TMC-114 (Johnson & Johnson), VX-385 (GW-640385; GSK/Vertex), VX-478 (Vertex/GSK).

The combinations, compositions, kit of parts, manufactures of this invention and the uses thereof of the above mentioned embodiments may be combined with further active ingredients.

Examples of such further active ingredients are acyclic nucleosides such as acyclovir, ganciclovir; interferons such as alpha-, beta- and gamma-interferon; glucuronation inhibitors such as probenecid; nucleoside transport inhibitors such as dipyridamole; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules and inhibitors of the HIV aspartyl protease such as L-735,524.

The compounds, or their pharmaceutically acceptable derivative or salts thereof, can also be mixed with other active materials that do not impair the desired action, or with materials that supplement the desired action, such as antibiotics, antifungals, antiinflammatorics, protease inhibitors, or other nucleoside or non-nucleoside antiviral agents, as discussed in more detail above.

In general, during alternation therapy, an effective dosage of each agent is administered serially, whereas in combination therapy, an effective dosage of two or more agents are administered together. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for tipranavir, compounds of formula (I), preferably 3'-deoxy-3'-fluorothymidine, ritonavir, further NRTIs and other antivirals can be found in the scientific literature. Many examples of suitable dosage ranges for other compounds described herein are also found in the public literature or can be identified using known procedures. These dosage ranges can be modified as desired to achieve a desired result.

It has been recognized that drug-resistant variants of HIV can emerge after prolonged treatment with an antiviral agent. Drug resistance most typically occurs by mutation of a gene that encodes for an enzyme used in the viral life cycle, and most typically in the case of HIV, in either the reverse transcriptase or protease genes. It has been demonstrated that the efficacy of a drug against HIV infection can be prolonged, augmented, or restored by administering the compound in combination or alternation with a second, and perhaps third, antiviral compound that induces a different mutation(s) from that selected for by the principle drug. Alternatively, the pharmacokinetics, biodistribution, or other parameter of the drug can be altered by such combination or alternation therapy. In general, combination therapy is typically preferred over alternation therapy because it induces-multiple simultaneous stresses on the virus. In the case of administering the antiviral compounds in alternation, i.e. sequentially, the time gap between administering the first compound and the second compound is preferably not too long in order to achieve a beneficial effect. Preferably, the time gap is less than half a day, most preferably less than 6 hours.

While it is possible that, for use in therapy, a compound of the invention may be administered as the raw chemical it is preferable to present the active ingredient as a pharmaceutical formulation. The invention thus further provides a pharmaceutical formulation comprising tipranavir and a compound of the formula (I) with one or more pharmaceutically acceptable carriers and, optionally, other therapeutic and/or prophylactic ingredients.

Pharmaceutical formulations include those suitable for oral, rectal, nasal, topical (including buccal and sub lingual), transdermal, vaginal or parenteral (including intramuscular, sub-cutaneous and intravenous) administration in liquid or solid form or in a form suitable for administration by inhalation or insufflation. The formulations may, where appropriate, be conveniently presented in discrete dosage units and may be prepared by any of the methods well known in the art of pharmacy. All methods include the step of bringing into association the active compound(s) with liquid carriers or finely divided solid carriers or both and then, if necessary, shaping the product into the desired formulation.

Pharmaceutical formulation suitable for oral administration may conveniently be presented as discrete units such as capsules, including soft gelatin capsules, cachets or tablets each containing a predetermined amount of the active ingredient(s); as a powder or granules; as a solution, a suspension or as an emulsion, for example as syrups, elixirs or self-emulsifying delivery systems (SEDDS). The active ingredient(s) may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient(s) may be in powder form, obtained by aseptic isolation of sterile solid or by lyophilisation from solution, for constitution with a suitable vehicle, e.g. sterile, pyrogen-free water, before use.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

When desired the above described formulations adapted to give sustained release of the active ingredient(s) may be employed.

The compositions, combinations, kit of parts, manufacture and/or the use of the combinations according to this invention are advantageous in the treatment and/or prophylaxis of viral infections in a patient, preferably human retrovirus (HRV) infections and hepatitis B, in particular HIV infections, especially multiresistant HIV infections. Therefore this invention may offer an aid especially for highly treatment experienced patients suffering from multi-resistant HIV. In addition to the treatment of said diseases, the combinations, formulations and compositions according to this invention can be used prophylactically to prevent or retard the progression of clinical illness in individuals who are anti-HIV antibody or HIV-antigen positive or who have been exposed to HIV.

The compositions, combinations, kit of parts, manufacture and/or the use of the combinations according to this invention may also be beneficial in preventing perinatal transmission of human retroviral (HRV) infections, in particular HIV-1, from mother to baby. According to this method, tipranavir and a compound of the formula (I), preferably 3'-deoxy-3'-fluorothymidine, and optionally further active compounds as described hereinbefore or hereinafter are administered in combination or alternation to the mother before giving birth.

The compositions, combinations, kit of parts, manufacture and/or the use of the combinations according to this invention may also be beneficial in the treatment and/or prophylaxis of other HIV/AIDS-related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections.

Therefore, patients to be treated would be especially those individuals:

1) infected with one or more strains of a human retrovirus as determined by the presence of either measurable viral antibody or antigen in the serum; and/or
2) in the case of HIV, having either a asymptomatic HIV infection or a symptomatic AIDS defining infection such as i) disseminated histoplasmosis, ii) isopsoriasis, iii) bronchial and pulmonary candidiasis including pneumocystic pneumonia, iv) non-Hodgkin's lymphoma or v) Kaposi's sarcoma and being less than sixty years old; or having an absolute CD4+ lymphocyte count of less than 500/mm$^3$ in the peripheral blood.

The pharmaceutical combination according to this invention can be tested for additive and synergistic activity against HIV according to a number of assays known in scientific and public literature, including the one described in the WO 98/44913 and WO 00/51641, which are included herein by way of reference.

The present invention is illustrated in further detail by the following non-limiting examples of combinations according to this invention, comprising a 1$^{st}$ compound, a 2$^{nd}$ compound, optionally a 3$^{rd}$ compound, optionally a 4$^{th}$ compound and optionally a 5$^{th}$ compound.

Table 1 illustrating combinations of a compound of the formula (I), tipranavir (TPV) and one, two or more further NRTIs

| 1$^{st}$ compound | 2$^{nd}$ compound | 3$^{rd}$ compound | 4$^{th}$ compound |
|---|---|---|---|
| FLT | TPV | Abacavir Sulfate | |
| FLT | TPV | Didanosine | |
| FLT | TPV | Emtricitabine | |
| FLT | TPV | Lamivudine | |
| FLT | TPV | Stavudine | |
| FLT | TPV | Tenofovir disoproxil fumarate | |
| FLT | TPV | Zalcitabine | |
| FLT | TPV | Zidovudine | |
| FLT | TPV | Amdoxovir | |
| FLT | TPV | Elvucitabine | |
| FLT | TPV | GS-7340 | |
| FLT | TPV | INK-20 | |
| FLT | TPV | MIV-210 | |
| FLT | TPV | Racivir | |
| FLT | TPV | Reverset | |
| FLT | TPV | SPD-754 | |
| FLT | TPV | BCH-13520 | |
| FLT | TPV | BCH-10618 | |
| FLT | TPV | Ritonavir | Abacavir Sulfate |
| FLT | TPV | Ritonavir | Didanosine |
| FLT | TPV | Ritonavir | Emtricitabine |
| FLT | TPV | Ritonavir | Lamivudine |
| FLT | TPV | Ritonavir | Stavudine |
| FLT | TPV | Ritonavir | Tenofovir disoproxil fumarate |
| FLT | TPV | Ritonavir | Zalcitabine |
| FLT | TPV | Ritonavir | Zidovudine |
| FLT | TPV | Ritonavir | Amdoxovir |
| FLT | TPV | Ritonavir | Elvucitabine |
| FLT | TPV | Ritonavir | GS-7340 |
| FLT | TPV | Ritonavir | INK-20 |
| FLT | TPV | Ritonavir | MIV-210 |
| FLT | TPV | Ritonavir | Racivir |
| FLT | TPV | Ritonavir | Reverset |
| FLT | TPV | Ritonavir | SPD-754 |
| FLT | TPV | Ritonavir | BCH-13520 |
| FLT | TPV | Ritonavir | BCH-10618 |
| FLG | TPV | Abacavir Sulfate | |
| FLG | TPV | Didanosine | |
| FLG | TPV | Emtricitabine | |
| FLG | TPV | Lamivudine | |
| FLG | TPV | Stavudine | |
| FLG | TPV | Tenofovir disoproxil fumarate | |
| FLG | TPV | Zalcitabine | |
| FLG | TPV | Zidovudine | |
| FLG | TPV | Amdoxovir | |
| FLG | TPV | Elvucitabine | |
| FLG | TPV | GS-7340 | |
| FLG | TPV | INK-20 | |
| FLG | TPV | MIV-310 | |
| FLG | TPV | Racivir | |
| FLG | TPV | Reverset | |
| FLG | TPV | SPD-754 | |
| FLG | TPV | BCH-13520 | |
| FLG | TPV | BCH-10618 | |
| FLG | TPV | Ritonavir | Abacavir Sulfate |
| FLG | TPV | Ritonavir | Didanosine |
| FLG | TPV | Ritonavir | Emtricitabine |
| FLG | TPV | Ritonavir | Lamivudine |
| FLG | TPV | Ritonavir | Stavudine |
| FLG | TPV | Ritonavir | Tenofovir disoproxil fumarate |
| FLG | TPV | Ritonavir | Zalcitabine |
| FLG | TPV | Ritonavir | Zidovudine |
| FLG | TPV | Ritonavir | Amdoxovir |
| FLG | TPV | Ritonavir | Elvucitabine |
| FLG | TPV | Ritonavir | GS-7340 |
| FLG | TPV | Ritonavir | INK-20 |
| FLG | TPV | Ritonavir | MIV-310 |
| FLG | TPV | Ritonavir | Racivir |
| FLG | TPV | Ritonavir | Reverset |
| FLG | TPV | Ritonavir | SPD-754 |
| FLG | TPV | Ritonavir | BCH-13520 |
| FLG | TPV | Ritonavir | BCH-10618 |

Table 2 illustrating combinations of a compound of the formula (I), tipranavir, a NNRTI and optionally one, two or more further NRTIs

| 1$^{st}$ compound | 2$^{nd}$ compound | 3$^{rd}$ compound | 4$^{th}$ compound |
|---|---|---|---|
| FLT | TPV | Delavirdine | |
| FLT | TPV | Efavirenz | |
| FLT | TPV | Nevirapine | |
| FLT | TPV | (+)-Calanolide A or B | |
| FLT | TPV | Capravirine | |
| FLT | TPV | GW-695634 | |
| FLT | TPV | MIV-150 | |
| FLT | TPV | MV026048 | |
| FLT | TPV | NV-05 | |
| FLT | TPV | R-278474 | |
| FLT | TPV | RS-1588 | |
| FLT | TPV | TMC-120/125 | |
| FLT | TPV | TMC-125 | |

-continued

| 1st compound | 2nd compound | 3rd compound | 4th compound |
|---|---|---|---|
| FLT | TPV | UC-781 | |
| FLT | TPV | YM-215389 | |
| FLT | TPV | Ritonavir | Delavirdine |
| FLT | TPV | Ritonavir | Efavirenz |
| FLT | TPV | Ritonavir | Nevirapine |
| FLT | TPV | Ritonavir | (+)-Calanolide A or B |
| FLT | TPV | Ritonavir | Capravirine |
| FLT | TPV | Ritonavir | GW-695634 |
| FLT | TPV | Ritonavir | MIV-150 |
| FLT | TPV | Ritonavir | MV026048 |
| FLT | TPV | Ritonavir | NV-05 |
| FLT | TPV | Ritonavir | R-278474 |
| FLT | TPV | Ritonavir | RS-1588 |
| FLT | TPV | Ritonavir | TMC-120/125 |
| FLT | TPV | Ritonavir | TMC-125 |
| FLT | TPV | Ritonavir | UC-781 |
| FLT | TPV | Ritonavir | YM-215389 |
| FLG | TPV | Delavirdine | |
| FLG | TPV | Efavirenz | |
| FLG | TPV | Nevirapine | |
| FLG | TPV | (+)-Calanolide A or B | |
| FLG | TPV | Capravirine | |
| FLG | TPV | GW-695634 | |
| FLG | TPV | MIV-150 | |
| FLG | TPV | MV026048 | |
| FLG | TPV | NV-05 | |
| FLG | TPV | R-278474 | |
| FLG | TPV | RS-1588 | |
| FLG | TPV | TMC-120/125 | |
| FLG | TPV | TMC-125 | |
| FLG | TPV | UC-781 | |
| FLG | TPV | YM-215389 | |
| FLG | TPV | Ritonavir | Delavirdine |
| FLG | TPV | Ritonavir | Efavirenz |
| FLG | TPV | Ritonavir | Nevirapine |
| FLG | TPV | Ritonavir | (+)-Calanolide A or B |
| FLG | TPV | Ritonavir | Capravirine |
| FLG | TPV | Ritonavir | GW-695634 |
| FLG | TPV | Ritonavir | MIV-150 |
| FLG | TPV | Ritonavir | MV026048 |
| FLG | TPV | Ritonavir | NV-05 |
| FLG | TPV | Ritonavir | R-278474 |
| FLG | TPV | Ritonavir | RS-1588 |
| FLG | TPV | Ritonavir | TMC-120/125 |
| FLG | TPV | Ritonavir | TMC-125 |
| FLG | TPV | Ritonavir | UC-781 |
| FLG | TPV | Ritonavir | YM-215389 |

Table 3 illustrating combinations of a compound of the formula (I), tipranavir, an entry inhibitor and optionally one, two or more further NRTIs

| 1st compound | 2nd compound | 3rd compound | 4th compound |
|---|---|---|---|
| FLT | TPV | Enfurvirtide | |
| FLT | TPV | T-1249 | |
| FLT | TPV | AMD-070 | |
| FLT | TPV | BlockAide/CR | |
| FLT | TPV | BMS 806 | |
| FLT | TPV | KRH-1636 | |
| FLT | TPV | ONO-4128 | |
| FLT | TPV | Pro-140 | |
| FLT | TPV | PRO-542 | |
| FLT | TPV | SCH-D | |
| FLT | TPV | TAK-220 | |
| FLT | TPV | TNX-355 | |
| FLT | TPV | UK-427,857 | |
| FLT | TPV | Ritonavir | Enfurvirtide |
| FLT | TPV | Ritonavir | T-1249 |
| FLT | TPV | Ritonavir | AMD-070 |
| FLT | TPV | Ritonavir | BlockAide/CR |
| FLT | TPV | Ritonavir | BMS 806 |
| FLT | TPV | Ritonavir | KRH-1636 |
| FLT | TPV | Ritonavir | ONO-4128 |
| FLT | TPV | Ritonavir | Pro-140 |
| FLT | TPV | Ritonavir | PRO-542 |
| FLT | TPV | Ritonavir | SCH-D |
| FLT | TPV | Ritonavir | TAK-220 |
| FLT | TPV | Ritonavir | TNX-355 |
| FLT | TPV | Ritonavir | UK-427,857 |
| FLG | TPV | Enfurvirtide | |
| FLG | TPV | T-1249 | |
| FLG | TPV | AMD-070 | |
| FLG | TPV | BlockAide/CR | |
| FLG | TPV | BMS 806 | |
| FLG | TPV | KRH-1636 | |
| FLG | TPV | ONO-4128 | |
| FLG | TPV | Pro-140 | |
| FLG | TPV | PRO-542 | |
| FLG | TPV | SCH-D | |
| FLG | TPV | TAK-220 | |
| FLG | TPV | TNX-355 | |
| FLG | TPV | UK-427,857 | |
| FLG | TPV | Ritonavir | Enfurvirtide |
| FLG | TPV | Ritonavir | T-1249 |
| FLG | TPV | Ritonavir | AMD-070 |
| FLG | TPV | Ritonavir | BlockAide/CR |
| FLG | TPV | Ritonavir | BMS 806 |
| FLG | TPV | Ritonavir | KRH-1636 |
| FLG | TPV | Ritonavir | ONO-4128 |
| FLG | TPV | Ritonavir | Pro-140 |
| FLG | TPV | Ritonavir | PRO-542 |
| FLG | TPV | Ritonavir | SCH-D |
| FLG | TPV | Ritonavir | TAK-220 |
| FLG | TPV | Ritonavir | TNX-355 |
| FLG | TPV | Ritonavir | UK-427,857 |

Table 4 illustrating combinations of a compound of the formula (I), tipranavir, a NNRTI, an entry inhibitor and optionally one, two or more further NRTIs

| 1st compound | 2nd compound | 3rd compound | 4th compound | 5th compound |
|---|---|---|---|---|
| FLT | TPV | Delavirdine | Enfurvirtide | |
| FLT | TPV | Delavirdine | T-1249 | |
| FLT | TPV | Delavirdine | AMD-070 | |
| FLT | TPV | Delavirdine | BlockAide/CR | |
| FLT | TPV | Delavirdine | BMS 806 | |
| FLT | TPV | Delavirdine | KRH-1636 | |
| FLT | TPV | Delavirdine | ONO-4128 | |
| FLT | TPV | Delavirdine | Pro-140 | |
| FLT | TPV | Delavirdine | PRO-542 | |
| FLT | TPV | Delavirdine | SCH-D | |
| FLT | TPV | Delavirdine | TAK-220 | |
| FLT | TPV | Delavirdine | TNX-355 | |
| FLT | TPV | Delavirdine | UK-427,857 | |
| FLT | TPV | Efavirenz | Enfurvirtide | |
| FLT | TPV | Efavirenz | T-1249 | |
| FLT | TPV | Efavirenz | AMD-070 | |
| FLT | TPV | Efavirenz | BlockAide/CR | |
| FLT | TPV | Efavirenz | BMS 806 | |
| FLT | TPV | Efavirenz | KRH-1636 | |
| FLT | TPV | Efavirenz | ONO-4128 | |
| FLT | TPV | Efavirenz | Pro-140 | |
| FLT | TPV | Efavirenz | PRO-542 | |
| FLT | TPV | Efavirenz | SCH-D | |
| FLT | TPV | Efavirenz | TAK-220 | |

-continued

| 1st compound | 2nd compound | 3rd compound | 4th compound | 5th compound |
|---|---|---|---|---|
| FLT | TPV | Efavirenz | TNX-355 | |
| FLT | TPV | Efavirenz | UK-427,857 | |
| FLT | TPV | Nevirapine | Enfurvirtide | |
| FLT | TPV | Nevirapine | T-1249 | |
| FLT | TPV | Nevirapine | AMD-070 | |
| FLT | TPV | Nevirapine | BlockAide/CR | |
| FLT | TPV | Nevirapine | BMS 806 | |
| FLT | TPV | Nevirapine | KRH-1636 | |
| FLT | TPV | Nevirapine | ONO-4128 | |
| FLT | TPV | Nevirapine | Pro-140 | |
| FLT | TPV | Nevirapine | PRO-542 | |
| FLT | TPV | Nevirapine | SCH-D | |
| FLT | TPV | Nevirapine | TAK-220 | |
| FLT | TPV | Nevirapine | TNX-355 | |
| FLT | TPV | Nevirapine | UK-427,857 | |
| FLT | TPV | GW-695634 | Enfurvirtide | |
| FLT | TPV | GW-695634 | T-1249 | |
| FLT | TPV | GW-695634 | AMD-070 | |
| FLT | TPV | GW-695634 | BlockAide/CR | |
| FLT | TPV | GW-695634 | BMS 806 | |
| FLT | TPV | GW-695634 | KRH-1636 | |
| FLT | TPV | GW-695634 | ONO-4128 | |
| FLT | TPV | GW-695634 | Pro-140 | |
| FLT | TPV | GW-695634 | PRO-542 | |
| FLT | TPV | GW-695634 | SCH-D | |
| FLT | TPV | GW-695634 | TAK-220 | |
| FLT | TPV | GW-695634 | TNX-355 | |
| FLT | TPV | GW-695634 | UK-427,857 | |
| FLT | TPV | Ritonavir | Delavirdine | Enfurvirtide |
| FLT | TPV | Ritonavir | Delavirdine | T-1249 |
| FLT | TPV | Ritonavir | Delavirdine | AMD-070 |
| FLT | TPV | Ritonavir | Delavirdine | BlockAide/CR |
| FLT | TPV | Ritonavir | Delavirdine | BMS 806 |
| FLT | TPV | Ritonavir | Delavirdine | KRH-1636 |
| FLT | TPV | Ritonavir | Delavirdine | ONO-4128 |
| FLT | TPV | Ritonavir | Delavirdine | Pro-140 |
| FLT | TPV | Ritonavir | Delavirdine | PRO-542 |
| FLT | TPV | Ritonavir | Delavirdine | SCH-D |
| FLT | TPV | Ritonavir | Delavirdine | TAK-220 |
| FLT | TPV | Ritonavir | Delavirdine | TNX-355 |
| FLT | TPV | Ritonavir | Delavirdine | UK-427,857 |
| FLT | TPV | Ritonavir | Efavirenz | Enfurvirtide |
| FLT | TPV | Ritonavir | Efavirenz | T-1249 |
| FLT | TPV | Ritonavir | Efavirenz | AMD-070 |
| FLT | TPV | Ritonavir | Efavirenz | BlockAide/CR |
| FLT | TPV | Ritonavir | Efavirenz | BMS 806 |
| FLT | TPV | Ritonavir | Efavirenz | KRH-1636 |
| FLT | TPV | Ritonavir | Efavirenz | ONO-4128 |
| FLT | TPV | Ritonavir | Efavirenz | Pro-140 |
| FLT | TPV | Ritonavir | Efavirenz | PRO-542 |
| FLT | TPV | Ritonavir | Efavirenz | SCH-D |
| FLT | TPV | Ritonavir | Efavirenz | TAK-220 |
| FLT | TPV | Ritonavir | Efavirenz | TNX-355 |
| FLT | TPV | Ritonavir | Efavirenz | UK-427,857 |
| FLT | TPV | Ritonavir | Nevirapine | Enfurvirtide |
| FLT | TPV | Ritonavir | Nevirapine | T-1249 |
| FLT | TPV | Ritonavir | Nevirapine | AMD-070 |
| FLT | TPV | Ritonavir | Nevirapine | BlockAide/CR |
| FLT | TPV | Ritonavir | Nevirapine | BMS 806 |
| FLT | TPV | Ritonavir | Nevirapine | KRH-1636 |
| FLT | TPV | Ritonavir | Nevirapine | ONO-4128 |
| FLT | TPV | Ritonavir | Nevirapine | Pro-140 |
| FLT | TPV | Ritonavir | Nevirapine | PRO-542 |
| FLT | TPV | Ritonavir | Nevirapine | SCH-D |
| FLT | TPV | Ritonavir | Nevirapine | TAK-220 |
| FLT | TPV | Ritonavir | Nevirapine | TNX-355 |
| FLT | TPV | Ritonavir | Nevirapine | UK-427,857 |
| FLT | TPV | Ritonavir | GW-695634 | Enfurvirtide |
| FLT | TPV | Ritonavir | GW-695634 | T-1249 |
| FLT | TPV | Ritonavir | GW-695634 | AMD-070 |
| FLT | TPV | Ritonavir | GW-695634 | BlockAide/CR |
| FLT | TPV | Ritonavir | GW-695634 | BMS 806 |
| FLT | TPV | Ritonavir | GW-695634 | KRH-1636 |
| FLT | TPV | Ritonavir | GW-695634 | ONO-4128 |
| FLT | TPV | Ritonavir | GW-695634 | Pro-140 |
| FLT | TPV | Ritonavir | GW-695634 | PRO-542 |
| FLT | TPV | Ritonavir | GW-695634 | SCH-D |
| FLT | TPV | Ritonavir | GW-695634 | TAK-220 |
| FLT | TPV | Ritonavir | GW-695634 | TNX-355 |
| FLT | TPV | Ritonavir | GW-695634 | UK-427,857 |
| FLG | TPV | Delavirdine | Enfurvirtide | |
| FLG | TPV | Delavirdine | T-1249 | |
| FLG | TPV | Delavirdine | AMD-070 | |
| FLG | TPV | Delavirdine | BlockAide/CR | |
| FLG | TPV | Delavirdine | BMS 806 | |
| FLG | TPV | Delavirdine | KRH-1636 | |
| FLG | TPV | Delavirdine | ONO-4128 | |
| FLG | TPV | Delavirdine | Pro-140 | |
| FLG | TPV | Delavirdine | PRO-542 | |
| FLG | TPV | Delavirdine | SCH-D | |
| FLG | TPV | Delavirdine | TAK-220 | |
| FLG | TPV | Delavirdine | TNX-355 | |
| FLG | TPV | Delavirdine | UK-427,857 | |
| FLG | TPV | Efavirenz | Enfurvirtide | |
| FLG | TPV | Efavirenz | T-1249 | |
| FLG | TPV | Efavirenz | AMD-070 | |
| FLG | TPV | Efavirenz | BlockAide/CR | |
| FLG | TPV | Efavirenz | BMS 806 | |
| FLG | TPV | Efavirenz | KRH-1636 | |
| FLG | TPV | Efavirenz | ONO-4128 | |
| FLG | TPV | Efavirenz | Pro-140 | |
| FLG | TPV | Efavirenz | PRO-542 | |
| FLG | TPV | Efavirenz | SCH-D | |
| FLG | TPV | Efavirenz | TAK-220 | |
| FLG | TPV | Efavirenz | TNX-355 | |
| FLG | TPV | Efavirenz | UK-427,857 | |
| FLG | TPV | Nevirapine | Enfurvirtide | |
| FLG | TPV | Nevirapine | T-1249 | |
| FLG | TPV | Nevirapine | AMD-070 | |
| FLG | TPV | Nevirapine | BlockAide/CR | |
| FLG | TPV | Nevirapine | BMS 806 | |
| FLG | TPV | Nevirapine | KRH-1636 | |
| FLG | TPV | Nevirapine | ONO-4128 | |
| FLG | TPV | Nevirapine | Pro-140 | |
| FLG | TPV | Nevirapine | PRO-542 | |
| FLG | TPV | Nevirapine | SCH-D | |
| FLG | TPV | Nevirapine | TAK-220 | |
| FLG | TPV | Nevirapine | TNX-355 | |
| FLG | TPV | Nevirapine | UK-427,857 | |
| FLG | TPV | GW-695634 | Enfurvirtide | |
| FLG | TPV | GW-695634 | T-1249 | |
| FLG | TPV | GW-695634 | AMD-070 | |
| FLG | TPV | GW-695634 | BlockAide/CR | |
| FLG | TPV | GW-695634 | BMS 806 | |
| FLG | TPV | GW-695634 | KRH-1636 | |
| FLG | TPV | GW-695634 | ONO-4128 | |
| FLG | TPV | GW-695634 | Pro-140 | |
| FLG | TPV | GW-695634 | PRO-542 | |
| FLG | TPV | GW-695634 | SCH-D | |
| FLG | TPV | GW-695634 | TAK-220 | |
| FLG | TPV | GW-695634 | TNX-355 | |
| FLG | TPV | GW-695634 | UK-427,857 | |
| FLG | TPV | Ritonavir | Delavirdine | Enfurvirtide |
| FLG | TPV | Ritonavir | Delavirdine | T-1249 |
| FLG | TPV | Ritonavir | Delavirdine | AMD-070 |
| FLG | TPV | Ritonavir | Delavirdine | BlockAide/CR |
| FLG | TPV | Ritonavir | Delavirdine | BMS 806 |
| FLG | TPV | Ritonavir | Delavirdine | KRH-1636 |
| FLG | TPV | Ritonavir | Delavirdine | ONO-4128 |
| FLG | TPV | Ritonavir | Delavirdine | Pro-140 |
| FLG | TPV | Ritonavir | Delavirdine | PRO-542 |
| FLG | TPV | Ritonavir | Delavirdine | SCH-D |
| FLG | TPV | Ritonavir | Delavirdine | TAK-220 |
| FLG | TPV | Ritonavir | Delavirdine | TNX-355 |
| FLG | TPV | Ritonavir | Delavirdine | UK-427,857 |
| FLG | TPV | Ritonavir | Efavirenz | Enfurvirtide |
| FLG | TPV | Ritonavir | Efavirenz | T-1249 |
| FLG | TPV | Ritonavir | Efavirenz | AMD-070 |
| FLG | TPV | Ritonavir | Efavirenz | BlockAide/CR |
| FLG | TPV | Ritonavir | Efavirenz | BMS 806 |
| FLG | TPV | Ritonavir | Efavirenz | KRH-1636 |
| FLG | TPV | Ritonavir | Efavirenz | ONO-4128 |

-continued

| 1st compound | 2nd compound | 3rd compound | 4th compound | 5th compound |
|---|---|---|---|---|
| FLG | TPV | Ritonavir | Efavirenz | Pro-140 |
| FLG | TPV | Ritonavir | Efavirenz | PRO-542 |
| FLG | TPV | Ritonavir | Efavirenz | SCH-D |
| FLG | TPV | Ritonavir | Efavirenz | TAK-220 |
| FLG | TPV | Ritonavir | Efavirenz | TNX-355 |
| FLG | TPV | Ritonavir | Efavirenz | UK-427,857 |
| FLG | TPV | Ritonavir | Nevirapine | Enfurvirtide |
| FLG | TPV | Ritonavir | Nevirapine | T-1249 |
| FLG | TPV | Ritonavir | Nevirapine | AMD-070 |
| FLG | TPV | Ritonavir | Nevirapine | BlockAide/CR |
| FLG | TPV | Ritonavir | Nevirapine | BMS 806 |
| FLG | TPV | Ritonavir | Nevirapine | KRH-1636 |
| FLG | TPV | Ritonavir | Nevirapine | ONO-4128 |
| FLG | TPV | Ritonavir | Nevirapine | Pro-140 |
| FLG | TPV | Ritonavir | Nevirapine | PRO-542 |
| FLG | TPV | Ritonavir | Nevirapine | SCH-D |
| FLG | TPV | Ritonavir | Nevirapine | TAK-220 |
| FLG | TPV | Ritonavir | Nevirapine | TNX-355 |
| FLG | TPV | Ritonavir | Nevirapine | UK-427,857 |
| FLG | TPV | Ritonavir | GW-695634 | Enfurvirtide |
| FLG | TPV | Ritonavir | GW-695634 | T-1249 |
| FLG | TPV | Ritonavir | GW-695634 | AMD-070 |
| FLG | TPV | Ritonavir | GW-695634 | BlockAide/CR |
| FLG | TPV | Ritonavir | GW-695634 | BMS 806 |
| FLG | TPV | Ritonavir | GW-695634 | KRH-1636 |
| FLG | TPV | Ritonavir | GW-695634 | ONO-4128 |
| FLG | TPV | Ritonavir | GW-695634 | Pro-140 |
| FLG | TPV | Ritonavir | GW-695634 | PRO-542 |
| FLG | TPV | Ritonavir | GW-695634 | SCH-D |
| FLG | TPV | Ritonavir | GW-695634 | TAK-220 |
| FLG | TPV | Ritonavir | GW-695634 | TNX-355 |
| FLG | TPV | Ritonavir | GW-695634 | UK-427,857 |

Table 5 illustrating combinations of a compound of the formula (I), tipranavir, an integrase inhibitor and optionally one, two or more further NRTIs

| 1st compound | 2nd compound | 3rd compound | 4th compound |
|---|---|---|---|
| FLT | TPV | L-870810 | |
| FLT | TPV | c-2507 | |
| FLT | TPV | S(RSC)-1838 | |
| FLT | TPV | Ritonavir | L-870810 |
| FLT | TPV | Ritonavir | S(RSC)-1838 |
| FLG | TPV | L-870810 | |
| FLG | TPV | c-2507 | |
| FLG | TPV | S(RSC)-1838 | |
| FLG | TPV | Ritonavir | L-870810 |
| FLG | TPV | Ritonavir | S(RSC)-1838 |

Table 6 illustrating combinations of a compound of the formula (I), tipranavir, a NNRTI, an integrase inhibitor and optionally one, two or more further NRTIs

| 1st compound | 2nd compound | 3rd compound | 4th compound | 5th compound |
|---|---|---|---|---|
| FLT | TPV | Delavirdine | L-870810 | |
| FLT | TPV | Delavirdine | c-2507 | |
| FLT | TPV | Delavirdine | S(RSC)-1838 | |
| FLT | TPV | Efavirenz | L-870810 | |
| FLT | TPV | Efavirenz | S(RSC)-1838 | |
| FLT | TPV | Nevirapine | L-870810 | |
| FLT | TPV | Nevirapine | c-2507 | |
| FLT | TPV | Nevirapine | S(RSC)-1838 | |
| FLT | TPV | (+)-Calanolide A or B | S(RSC)-1838 | |
| FLT | TPV | (+)-Calanolide A or B | c-2507 | |
| FLT | TPV | (+)-Calanolide A or B | L-870810 | |
| FLT | TPV | Capravirine | S(RSC)-1838 | |
| FLT | TPV | Capravirine | L-870810 | |
| FLT | TPV | Capravirine | c-2507 | |
| FLT | TPV | GW-695634 | S(RSC)-1838 | |
| FLT | TPV | GW-695634 | L-870810 | |
| FLT | TPV | GW-695634 | c-2507 | |
| FLT | TPV | MIV-150 | S(RSC)-1838 | |
| FLT | TPV | MIV-150 | L-870810 | |
| FLT | TPV | MIV-150 | c-2507 | |
| FLT | TPV | MV026048 | S(RSC)-1838 | |
| FLT | TPV | NV-05 | L-870810 | |
| FLT | TPV | NV-05 | c-2507 | |
| FLT | TPV | NV-05 | S(RSC)-1838 | |
| FLT | TPV | R-278474 | L-870810 | |
| FLT | TPV | R-278474 | c-2507 | |
| FLT | TPV | R-278474 | S(RSC)-1838 | |
| FLT | TPV | RS-1588 | L-870810 | |
| FLT | TPV | RS-1588 | S(RSC)-1838 | |
| FLT | TPV | TMC-120/125 | S(RSC)-1838 | |
| FLT | TPV | TMC-120/125 | c-2507 | |
| FLT | TPV | TMC-120/125 | L-870810 | |
| FLT | TPV | TMC-125 | S(RSC)-1838 | |
| FLT | TPV | TMC-125 | L-870810 | |
| FLT | TPV | TMC-125 | c-2507 | |
| FLT | TPV | UC-781 | S(RSC)-1838 | |
| FLT | TPV | UC-781 | L-870810 | |
| FLT | TPV | UC-781 | c-2507 | |
| FLT | TPV | YM-215389 | S(RSC)-1838 | |
| FLT | TPV | YM-215389 | L-870810 | |
| FLT | TPV | YM-215389 | c-2507 | |
| FLT | TPV | Ritonavir | Delavirdine | L-870810 |
| FLT | TPV | Ritonavir | Delavirdine | S(RSC)-1838 |
| FLT | TPV | Ritonavir | Efavirenz | L-870810 |
| FLT | TPV | Ritonavir | Efavirenz | S(RSC)-1838 |
| FLT | TPV | Ritonavir | Nevirapine | L-870810 |
| FLT | TPV | Ritonavir | Nevirapine | S(RSC)-1838 |
| FLT | TPV | Ritonavir | (+)-Calanolide A or B | S(RSC)-1838 |
| FLT | TPV | Ritonavir | (+)-Calanolide A or B | L-870810 |
| FLT | TPV | Ritonavir | Capravirine | S(RSC)-1838 |
| FLT | TPV | Ritonavir | Capravirine | L-870810 |
| FLT | TPV | Ritonavir | GW-695634 | S(RSC)-1838 |
| FLT | TPV | Ritonavir | GW-695634 | L-870810 |
| FLT | TPV | Ritonavir | MIV-150 | S(RSC)-1838 |
| FLT | TPV | Ritonavir | MIV-150 | L-870810 |
| FLT | TPV | Ritonavir | MV026048 | S(RSC)-1838 |
| FLT | TPV | Ritonavir | NV-05 | L-870810 |
| FLT | TPV | Ritonavir | NV-05 | S(RSC)-1838 |
| FLT | TPV | Ritonavir | R-278474 | L-870810 |
| FLT | TPV | Ritonavir | R-278474 | S(RSC)-1838 |
| FLT | TPV | Ritonavir | RS-1588 | L-870810 |
| FLT | TPV | Ritonavir | RS-1588 | S(RSC)-1838 |
| FLT | TPV | Ritonavir | TMC-120/125 | S(RSC)-1838 |
| FLT | TPV | Ritonavir | TMC-120/125 | L-870810 |
| FLT | TPV | Ritonavir | TMC-125 | S(RSC)-1838 |
| FLT | TPV | Ritonavir | TMC-125 | L-870810 |
| FLT | TPV | Ritonavir | UC-781 | S(RSC)-1838 |
| FLT | TPV | Ritonavir | UC-781 | L-870810 |
| FLT | TPV | Ritonavir | YM-215389 | S(RSC)-1838 |
| FLT | TPV | Ritonavir | YM-215389 | L-870810 |
| FLG | TPV | Delavirdine | L-870810 | |
| FLG | TPV | Delavirdine | S(RSC)-1838 | |
| FLG | TPV | Efavirenz | L-870810 | |

-continued

| 1st compound | 2nd compound | 3rd compound | 4th compound | 5th compound |
|---|---|---|---|---|
| FLG | TPV | Efavirenz | S(RSC)-1838 | |
| FLG | TPV | Nevirapine | L-870810 | |
| FLG | TPV | Nevirapine | S(RSC)-1838 | |
| FLG | TPV | (+)-Calanolide A or B | S(RSC)-1838 | |
| FLG | TPV | (+)-Calanolide A or B | L-870810 | |
| FLG | TPV | Capravirine | S(RSC)-1838 | |
| FLG | TPV | Capravirine | L-870810 | |
| FLG | TPV | GW-695634 | S(RSC)-1838 | |
| FLG | TPV | GW-695634 | L-870810 | |
| FLG | TPV | MIV-150 | S(RSC)-1838 | |
| FLG | TPV | MIV-150 | L-870810 | |
| FLG | TPV | MV026048 | S(RSC)-1838 | |
| FLG | TPV | NV-05 | L-870810 | |
| FLG | TPV | NV-05 | S(RSC)-1838 | |
| FLG | TPV | R-278474 | L-870810 | |
| FLG | TPV | R-278474 | S(RSC)-1838 | |
| FLG | TPV | RS-1588 | L-870810 | |
| FLG | TPV | RS-1588 | S(RSC)-1838 | |
| FLG | TPV | TMC-120/125 | S(RSC)-1838 | |
| FLG | TPV | TMC-120/125 | L-870810 | |
| FLG | TPV | TMC-125 | S(RSC)-1838 | |
| FLG | TPV | TMC-125 | L-870810 | |
| FLG | TPV | UC-781 | S(RSC)-1838 | |
| FLG | TPV | UC-781 | L-870810 | |
| FLG | TPV | YM-215389 | S(RSC)-1838 | |
| FLG | TPV | YM-215389 | L-870810 | |
| FLG | TPV | Ritonavir | Delavirdine | L-870810 |
| FLG | TPV | Ritonavir | Delavirdine | S(RSC)-1838 |
| FLG | TPV | Ritonavir | Efavirenz | L-870810 |
| FLG | TPV | Ritonavir | Efavirenz | S(RSC)-1838 |
| FLG | TPV | Ritonavir | Nevirapine | L-870810 |
| FLG | TPV | Ritonavir | Nevirapine | S(RSC)-1838 |
| FLG | TPV | Ritonavir | (+)-Calanolide A or B | S(RSC)-1838 |
| FLG | TPV | Ritonavir | (+)-Calanolide A or B | L-870810 |
| FLG | TPV | Ritonavir | Capravirine | S(RSC)-1838 |
| FLG | TPV | Ritonavir | Capravirine | L-870810 |
| FLG | TPV | Ritonavir | GW-695634 | S(RSC)-1838 |
| FLG | TPV | Ritonavir | GW-695634 | L-870810 |
| FLG | TPV | Ritonavir | MIV-150 | S(RSC)-1838 |
| FLG | TPV | Ritonavir | MIV-150 | L-870810 |
| FLG | TPV | Ritonavir | MV026048 | S(RSC)-1838 |
| FLG | TPV | Ritonavir | NV-05 | L-870810 |
| FLG | TPV | Ritonavir | NV-05 | S(RSC)-1838 |
| FLG | TPV | Ritonavir | R-278474 | L-870810 |
| FLG | TPV | Ritonavir | R-278474 | S(RSC)-1838 |
| FLG | TPV | Ritonavir | RS-1588 | L-870810 |
| FLG | TPV | Ritonavir | RS-1588 | S(RSC)-1838 |
| FLG | TPV | Ritonavir | TMC-120/125 | S(RSC)-1838 |
| FLG | TPV | Ritonavir | TMC-120/125 | L-870810 |
| FLG | TPV | Ritonavir | TMC-125 | S(RSC)-1838 |
| FLG | TPV | Ritonavir | TMC-125 | L-870810 |
| FLG | TPV | Ritonavir | UC-781 | S(RSC)-1838 |
| FLG | TPV | Ritonavir | UC-781 | L-870810 |
| FLG | TPV | Ritonavir | YM-215389 | S(RSC)-1838 |
| FLG | TPV | Ritonavir | YM-215389 | L-870810 |

Table 7 illustrating combinations of a compound of the formula (I), tipranavir and a further antiviral

| 1st compound | 2nd compound | 3rd compound | 4th compound |
|---|---|---|---|
| FLT | TPV | PA-457 | |
| FLT | TPV | KPC-2 | |
| FLT | TPV | HGTV-43 | |
| FLT | TPV | Amprenavir | |
| FLT | TPV | Atazanavir | |
| FLT | TPV | Indinavir Sulfate | |
| FLT | TPV | Lexiva | |
| FLT | TPV | Lopinavir | |
| FLT | TPV | Nelfinavir Mesylate | |
| FLT | TPV | Saquinavir | |
| FLT | TPV | AG-1776 | |
| FLT | TPV | AG-1859 | |
| FLT | TPV | DPC-681/684 | |
| FLT | TPV | GS224338 | |
| FLT | TPV | KNI-272 | |
| FLT | TPV | Nar-DG-35 | |
| FLT | TPV | P(PL)-100 | |
| FLT | TPV | P-1946 | |
| FLT | TPV | R-944 | |
| FLT | TPV | RO-0334649 | |
| FLT | TPV | TMC-114 | |
| FLT | TPV | VX-385 | |
| FLT | TPV | VX-478 | |
| FLT | TPV | ritonavir | PA-457 |
| FLT | TPV | ritonavir | KPC-2 |
| FLT | TPV | ritonavir | HGTV-43 |
| FLT | TPV | ritonavir | Amprenavir |
| FLT | TPV | ritonavir | Atazanavir |
| FLT | TPV | ritonavir | Indinavir Sulfate |
| FLT | TPV | ritonavir | Lexiva |
| FLT | TPV | ritonavir | Lopinavir |
| FLT | TPV | ritonavir | Nelfinavir Mesylate |
| FLT | TPV | ritonavir | Saquinavir |
| FLT | TPV | ritonavir | AG-1776 |
| FLT | TPV | ritonavir | AG-1859 |
| FLT | TPV | ritonavir | DPC-681/684 |
| FLT | TPV | ritonavir | GS224338 |
| FLT | TPV | ritonavir | KNI-272 |
| FLT | TPV | ritonavir | Nar-DG-35 |
| FLT | TPV | ritonavir | P(PL)-100 |
| FLT | TPV | ritonavir | P-1946 |
| FLT | TPV | ritonavir | R-944 |
| FLT | TPV | ritonavir | RO-0334649 |
| FLT | TPV | ritonavir | TMC-114 |
| FLT | TPV | ritonavir | VX-385 |
| FLT | TPV | ritonavir | VX-478 |
| FLG | TPV | PA-457 | |
| FLG | TPV | KPC-2 | |
| FLG | TPV | HGTV-43 | |
| FLG | TPV | Amprenavir | |
| FLG | TPV | Atazanavir | |
| FLG | TPV | Indinavir Sulfate | |
| FLG | TPV | Lexiva | |
| FLG | TPV | Lopinavir | |
| FLG | TPV | Nelfinavir Mesylate | |
| FLG | TPV | Saquinavir | |
| FLG | TPV | AG-1776 | |
| FLG | TPV | AG-1859 | |
| FLG | TPV | DPC-681/684 | |
| FLG | TPV | GS224338 | |
| FLG | TPV | KNI-272 | |
| FLG | TPV | Nar-DG-35 | |
| FLG | TPV | P(PL)-100 | |
| FLG | TPV | P-1946 | |
| FLG | TPV | R-944 | |
| FLG | TPV | RO-0334649 | |
| FLG | TPV | TMC-114 | |
| FLG | TPV | VX-385 | |
| FLG | TPV | VX-478 | |
| FLG | TPV | ritonavir | PA-457 |

-continued

| 1st compound | 2nd compound | 3rd compound | 4th compound |
|---|---|---|---|
| FLG | TPV | ritonavir | KPC-2 |
| FLG | TPV | ritonavir | HGTV-43 |
| FLG | TPV | ritonavir | Amprenavir |
| FLG | TPV | ritonavir | Atazanavir |
| FLG | TPV | ritonavir | Indinavir Sulfate |
| FLG | TPV | ritonavir | Lexiva |
| FLG | TPV | ritonavir | Lopinavir |
| FLG | TPV | ritonavir | Nelfinavir Mesylate |
| FLG | TPV | ritonavir | Saquinavir |
| FLG | TPV | ritonavir | AG-1776 |
| FLG | TPV | ritonavir | AG-1859 |
| FLG | TPV | ritonavir | DPC-681/684 |
| FLG | TPV | ritonavir | GS224338 |
| FLG | TPV | ritonavir | KNI-272 |
| FLG | TPV | ritonavir | Nar-DG-35 |
| FLG | TPV | ritonavir | P(PL)-100 |
| FLG | TPV | ritonavir | P-1946 |
| FLG | TPV | ritonavir | R-944 |
| FLG | TPV | ritonavir | RO-0334649 |
| FLG | TPV | ritonavir | TMC-114 |
| FLG | TPV | ritonavir | VX-385 |
| FLG | TPV | ritonavir | VX-478 |

In the above given Tables 1 to 7 the term "FLG" is 2',3'-dideoxy-3'-fluoroguanosine, or a pharmaceutically acceptable salt or prodrug thereof, in particular 3'-deoxy-3'-fluoro-5-O-[2-(L-valyloxy)-propionyl]guanosine, or a pharmaceutically acceptable salt thereof.

What is claimed is:

1. A pharmaceutical composition for the treatment of an HIV or hepatitis B viral infection comprising tipranavir and at least one antiviral active compound selected from the group consisting of 3'-deoxy-3'-fluorothymidine, 2',3'-dideoxy-3'-fluoroguanosine, or 3'-deoxy-3'-fluoro-5-O-[2-(L-valyloxy)-propionyl]guanosine, or a pharmaceutically acceptable salt or prodrug thereof.

2. The pharmaceutical composition according to claim 1, wherein the antiviral active compound is 3'-deoxy-3'-fluorothymidine, or a pharmaceutically acceptable salt or prodrug thereof.

3. The pharmaceutical composition according to claim 1, wherein the antiviral active compound is 2',3'-dideoxy-3'-fluoroguanosine, or a pharmaceutically acceptable salt or prodrug thereof.

4. The pharmaceutical composition according to claim 1, wherein the antiviral active compound is 3'-deoxy-3'-fluoro-5-O-[2-(L-valyloxy)-propionyl]guanosine, or a pharmaceutically acceptable salt thereof.

5. The pharmaceutical composition according to claim 1, wherein tipranavir and the antiviral active compound are present in a ratio between about 1:250 to about 250:1.

6. The pharmaceutical composition according to claim 1 further comprising ritonavir.

7. The pharmaceutical composition according to claim 1 with at least one pharmaceutically acceptable carrier.

8. A method for treating an HIV or hepatitis B viral infection in an individual comprising administering tipranavir in combination or in alternation with at least one antiviral active compound selected from the group consisting of 3'-deoxy-3'-fluorothymidine, 2',3'-dideoxy-3'-fluoroguanosine, or 3'-deoxy-3'-fluoro-5-O-[2-(L-valyloxy)-propionyl]guanosine, or a pharmaceutically acceptable salt or prodrug thereof.

9. The method according to claim 8, wherein the antiviral active compound is 3'-deoxy-3'-fluorothymidine, or a pharmaceutically acceptable salt or prodrug thereof.

10. The method according to claim 8, wherein the antiviral active compound is 2',3'-dideoxy-3'-fluoroguanosine, or a pharmaceutically acceptable salt or prodrug thereof.

11. The method according to claim 8, wherein the antiviral active compound is 3'-deoxy-3'-fluoro-5-O-[2-(L-valyloxy)-propionyl]guanosine, or a pharmaceutically acceptable salt thereof.

12. The method according to claim 8, wherein tipranavir and the antiviral active compound are administered to the individual in combination or in alternation in a ratio between about 1:250 to about 250:1.

13. The method according to claim 8, wherein tipranavir and the antiviral active compound are administered to the individual in combination or in alternation in a ratio between about 1:50 to about 50:1.

14. The method according to claim 8, wherein tipranavir is administered in combination with ritonavir and in combination or in alternation with the antiviral active compound.

15. The method according to claim 8, wherein tipranavir is administered in combination with the antiviral active compound.

16. A kit for the treatment of an HIV or hepatitis B viral infection in an individual, comprising:
   (a) a first containment containing a pharmaceutical composition comprising tipranavir and at least one pharmaceutically acceptable carrier, and
   (b) a second containment containing a pharmaceutical composition comprising at least one antiviral active compound selected from the group consisting of 3'-deoxy-3'-fluorothymidine, 2,3'-dideoxy-3'-fluoroguanosine, or 3'-deoxy-3'-fluoro-5-O-[2-(L-valyloxy)-propionyl]guanosine, or a pharmaceutically acceptable salt or prodrug thereof, and at least one pharmaceutically acceptable carrier.

17. The kit according to claim 16, wherein the antiviral active compound is 3'-deoxy-3'-fluorothymidine, or a pharmaceutically acceptable salt or prodrug thereof.

18. The kit according to claim 16, wherein the antiviral active compound is 2',3'-dideoxy-3'-fluoroguanosine, or a pharmaceutically acceptable salt or prodrug thereof.

19. The kit according to claim 16, wherein the antiviral active compound is 3'-deoxy-3'-fluoro-5-O-[2-(L-valyloxy)-propionyl]guanosine, or a pharmaceutically acceptable salt thereof.

20. The kit according to claim 16, further comprising a containment containing a pharmaceutical composition comprising ritonavir.

* * * * *